(12) United States Patent
Chu et al.

(10) Patent No.: US 9,334,273 B1
(45) Date of Patent: May 10, 2016

(54) EFFICIENT AND STEREOSELECTIVE SYNTHESIS OF 2'-FLUORO-6'-METHYLENE-CARBOCYCLIC ADENOSINE (FMCA)

(71) Applicant: UNIVERSITY OF GEORGIA RESEARCH FOUNDATION, INC., Athens, GA (US)

(72) Inventors: David C. K. Chu, Stratham, GA (US); Uma S. Singh, Raebareliy (IN)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 0 days.

(21) Appl. No.: 14/631,209

(22) Filed: Feb. 25, 2015

Related U.S. Application Data

(60) Provisional application No. 61/948,234, filed on Mar. 5, 2014.

(51) Int. Cl.
*C07D 473/34* (2006.01)
*C07F 7/18* (2006.01)

(52) U.S. Cl.
CPC ............ *C07D 473/34* (2013.01); *C07F 7/1892* (2013.01)

(58) Field of Classification Search
CPC ..... C07D 473/34; C07F 7/1892; C07F 7/188; C07F 7/1876
See application file for complete search history.

(56) References Cited

U.S. PATENT DOCUMENTS

| | | | |
|---|---|---|---|
| 8,816,074 B2 | 8/2014 | Chu et al. | |
| 2011/0244027 A1* | 10/2011 | Chu et al. | 424/450 |
| 2014/0073606 A1 | 3/2014 | Chu et al. | |

FOREIGN PATENT DOCUMENTS

| | | |
|---|---|---|
| WO | 2008019124 A1 | 2/2008 |
| WO | 2011060408 A2 | 5/2011 |
| WO | 2012158552 A2 | 11/2012 |

OTHER PUBLICATIONS

Wuts, PGM, Greene's protective groups in organic synthesis. John Wiley & Sons, 2006; excerpt p. 356-358.*
Swamy, KCK, "Mitsunobu and related reactions: advances and applications." Chemical reviews 109.6 (2009): 2551-2651.*
www.who.int/mediacentre/factsheets/fs204/en/.
Bhattacharya, D.; Thio, C. L. Clinical Infectious Diseases 2010, 51, 1201.
Kim, K. H.; Kim, N. D.; Seong, B. L. Molecules 2010, 15, 5878.
Mukaide, M.; Tanaka, Y.; Shin-I, T.; Yuen, M. F.; Kurbanov, F.; Yokosuka, O.; Sata, M.; Karino, Y.; Yamada, G.; Sakaguchi, K.; Orito, E.; Inoue, M.; Baqai, S.; Lai, C. L.; Mizokami, M. Antimicrob. Agents Ch 2010, 54, 882.
Bartholomeusz, A.; Locarnini, S. Journal of Medical Virology 2006, 78, S52.
Wang, J. N.; Singh, U. S.; Rawal, R. K.; Sugiyama, M.; Yoo, J.; Jha, A. K; Scroggin, M.; Huang, Z. H.; Murray, M. G.; Govindarajan, R.; Tanaka, Y.; Korba, B.; Chu, C. K. Bioorg. Med. Chem. Lett. 2011, 21, 6328.
Rawal, R. K.; Singh, U. S.; Chavre, S. N.; Wang, J. N.; Sugiyama, M.; Hung, W.; Govindarajan, R.; Korba, B.; Tanaka, Y.; Chu, C. K. Bioorg. Med. Chem. Lett. 2013, 23, 503.
Walsh, A. W.; Langley, D. R.; Colonno, R. J.; Tenney, D. J. PLoS. One 2010, 5.
Jin, Y. H.; Liu, P.; Wang, J. N.; Baker, R.; Huggins, J.; Chu, C. K. J. Org. Chem. 2003, 68, 9012.
Jin, Y. H.; Chu, C. K. Nucleos. Nucleot. Nucl. 2003, 22, 771.
Gadthula, S.; Rawal, R. K.; Sharon, A.; Wu, D.; Korba, B.; Chu, C. K. Bioorg. Med. Chem. Lett. 2011, 21, 3982.
Vince, R.; Daluge, S.; Brownell, J. J. Med. Chem. 1986, 29, 2400.
Vince, R.; Hua, M. J. Med. Chem. 1990, 33, 17.
Daluge, S. M.; Martin, M. T.; Sickles, B. R.; Livingston, D. A. Nucleos. Nucleot. Nucl. 2000, 19, 297.
Corey, E. J.; Achiwa, K. J. Am. Chem. Soc. 1969, 91, 1429.
Mahmoudian, M.; Lowdon, A.; Jones, M.; Dawson, M.; Wallis, C. Tetrahedron-Asymmetr. 1999, 10, 1201.
Slama, J. T.; Mehta, N.; Skrzypczak-Jankun, E. J. Org. Chem. 2006, 71, 7877.
Grainger, R. S.; Patel, A. Chem. Commun. 2003, 1072.
Lakshmipathi, P.; Gree, D.; Gree, R. Org. Lett. 2002, 4, 451.
Alcaraz, L.; Cridland, A.; Kinchin, E. Org. Lett. 2001, 3, 4051.
Luche, J. L. J. Am. Chem. Soc. 1978, 100, 2226.

* cited by examiner

*Primary Examiner* — Samantha Shterengarts
*Assistant Examiner* — Matt Mauro
(74) *Attorney, Agent, or Firm* — Henry D. Coleman; R. Neil Sudol

(57) ABSTRACT

The invention provides a new convergent approach for the synthesis of 2'-fluoro-6'-methylene-carbocyclic adenosine (FMCA) from a readily available starting material (Vince lactam) in fourteen steps. An efficient and practical methodology for stereospecific preparation of a versatile carbocyclic key intermediate, D-2'-fluoro-6'-methylene cyclopentanol by diazotization, elimination, stereoselective epoxidation, fluorination and oxidative reduction of the Vince lactam in twelve steps is also provided.

2 Claims, 1 Drawing Sheet

EFFICIENT AND STEREOSELECTIVE SYNTHESIS OF 2'-FLUORO-6'-METHYLENE-CARBOCYCLIC ADENOSINE (FMCA)

RELATED APPLICATIONS

This application claims the benefit of priority of U.S. provisional application No. 61/948,234, filed 5 Mar. 2014 of identical title, the entire contents of which application is incorporated by reference herein.

FIELD OF THE INVENTION

The invention provides a new convergent approach for the synthesis of 2'-fluoro-6'-methylene-carbocyclic adenosine (FMCA) from a readily available starting material (Vince lactam) in fourteen steps. An efficient and practical methodology for stereospecific preparation of a versatile carbocyclic key intermediate, D-2'-fluoro-6'-methylene cyclopentanol by diazotization, elimination, stereoselective epoxidation, fluorination and oxidative reduction of the Vince lactam in twelve steps is also provided.

STATEMENT REGARDING FEDERAL FUNDING

There is no government support at this time.

BACKGROUND OF THE INVENTION

According to the world health organization (WHO) an estimated 2 billion people worldwide are infected with the hepatitis B Virus (HBV). More than 350 million patients live with chronic infection that results in 600,000 deaths worldwide every year.[1] Currently, there are several nucleos(t)ide analogues such as lamivudine, adefovir, telbivudine, entecavir, clevudine, and tenofovir have been demonstrated their clinical efficacy.[2,3]

Currently, entecavir and tenofovir are being prescribed as major anti-HBV agents for drug naïve as well as for the patients harboring adefovir and lamivudine resistant strains. However, the continuous use of entecavir also develops mutation, and particularly, in conjunction with lamivudine resistant mutation, entecavir becomes clinically ineffective.[4] Therefore, viral mutations limit the use of currently approved drugs as the anti-HBV therapy.[5] Thus, it is of great interest to discover anti-HBV agents, which are effective against drug-resistant HBV mutants As parts of our continued efforts to identify new and effective agents for HBV therapy, we discovered 2'-β-fluoro-6'-methylene carbocyclic adenosine (FMCA, 1)[6] and its phosphoramidate prodrug (FMCAP, 2)[7] (FIG. 1) as promising agents. FMCA and FMCAP demonstrated the anti-HBV efficacy in both wild type as well as resistant mutants. FMCA ($EC_{50}$ 0.67) and FMCAP ($EC_{50}$ 0.054) maintain their anti-HBV potency in vitro against the entecavir resistant triple mutant (L180M+M204V+S202G) while entecavir losses 150 fold less effective against the mutant in comparison to wild type.[8] To support ongoing biological and preclinical development, an efficient scale-up synthesis of FMCA was required.

Previously, we reported the synthesis of FMCA by a scheme which was long and tedious with an inefficient methodology from ribose for an initial discovery.[6] Although our group has been extensively involved in the synthesis of carbocyclic nucleosides from D-ribose,[9,10] this known procedure proves hazardous for a large scale preparation as an excess of MeI is required;[11] further, it has a low overall yield.[6]

SUMMARY OF THE INVENTION

The invention provides a new convergent approach for the synthesis of FMCA from a Vince lactam in fourteen steps. Our new convergent approach for efficient and scalable synthesis of FMCA in fourteen steps constitutes a highly efficient and practical method for making the key anti-HBV agent FMCA and avoids the drawbacks of the known, twenty-two step FMCA synthesis route.

In one embodiment, the invention provides a process for synthesizing a compound of the formula 1:

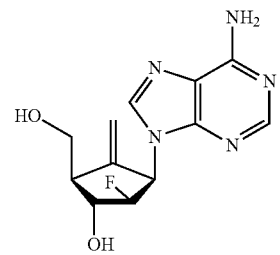

comprising coupling a β-allylic alcohol of formula 15:

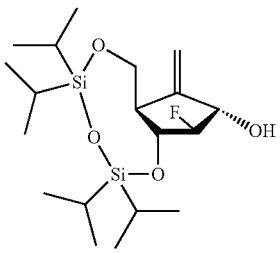

with protected adenine under Mitsunobu coupling conditions using diisopropyl azodicarboxylate (DIAD) and triphenylphosphine (TPP) in THF to produce a compound of formula 16, where P is an amine protecting group:

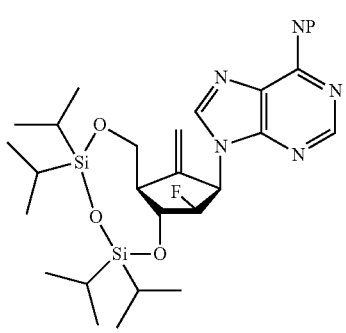

and removing P and the silyl protecting group of the compound of formula 16 to yield the compound of formula 1; wherein the process can be done one-pot or in steps.

Preferably, the amine protecting group P is tert-butyl carbamate (Boc) and the compound of formula 16 has the formula:

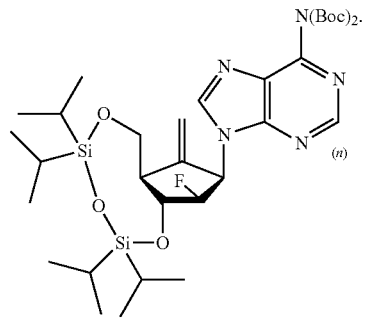

16

In another preferred embodiment, the Boc and silyl protecting groups of the compound of formula 16 are removed using tetrabutylammonium fluoride (TBAF) and trifluoroacetic acid (TFA) in THF at approximately room temperature.

In still another preferred embodiment, the invention provides a process for synthesizing a compound of the formula 1:

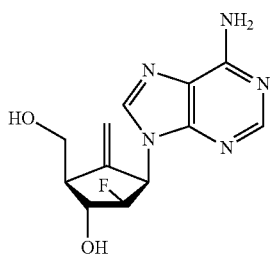

1 comprising the steps of:
(a) diazotization of an amine of formula 8:

8 followed by an elimination reaction to produce an alkene of formula 9:

9

(b) stereoselective epoxidation followed by fluorination of the alkene of formula 9 to yield a cis-fluoro β-epoxide of formula 13:

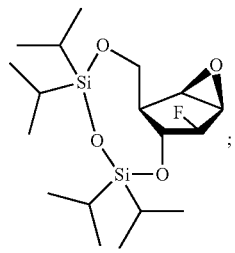

13

(c) selective opening of the cis-fluoro β-epoxide of the formula 13 to yield D-2'-fluoro-6'-methylene cyclopentenol of formula 15:

15 and coupling D-2'-fluoro-6'-methylene cyclopentenol of formula 15 with protected adenine under Mitsunobu coupling conditions using diisopropyl azodicarboxylate (DIAD) and triphenylphosphine (TPP) in THF to produce a compound of formula 16, where P is an amine protecting group:

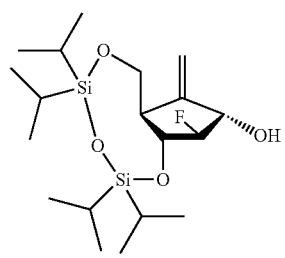

16 and
(d) removing P and the silyl protecting group of the compound of formula 16 to yield the compound of formula 1; wherein the process can be done one-pot or in steps.

In still another embodiment, the invention provides a process for synthesizing a compound of the formula 1:

1 comprising coupling D-2'-fluoro-6'-methylene cyclopentenol of formula 15:

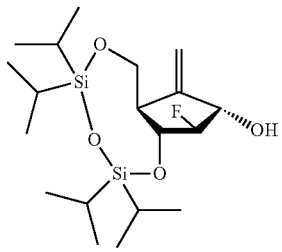
15 with protected adenine under Mitsunobu coupling conditions using diisopropyl azodicarboxylate (DIAD) and triphenylphosphine (TPP) in THF to produce a compound of formula 16, where P is an amine protecting group:

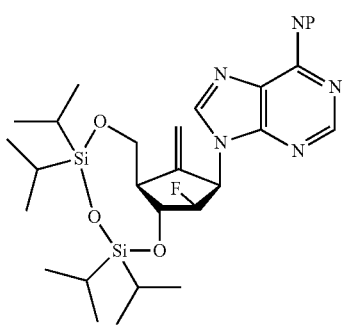
16 and removing P and the silyl protecting group of the compound of formula 16 to yield the compound of formula 1; wherein the D-2'-fluoro-6'-methylene cyclopentenol of formula 15 is made by a process which includes the step of reacting (1S)-(±)-2-azabicyclo[2.2.1]hept-5-en-3-one (3) (Vince lactam) with di-tert-butyl dicarbonate in the presence of a catalytic amount of 4-dimethylaminopyridine (DMAP) in THF to yield a N-Boc protected (±) γ-lactam 4:

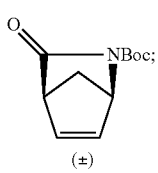
4 and wherein the process can be done one-pot or in steps.

The invention also includes novel intermediate synthesis steps which are encompassed by the processes described above. For example, the invention provides a process for making a β-allylic alcohol of formula 15:

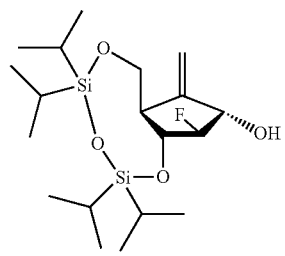
15 comprising oxidizing an allylic alcohol of the formula 14:

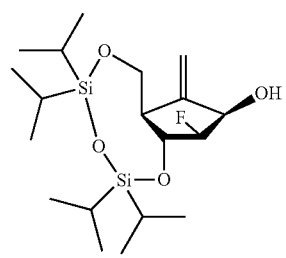
14 with a Dess-martin periodinane reagent at a temperature range of about −5° C. to about 5° C., most preferably at a temperature of about 0° C., to yield a cyclopentanone intermediate, and subjecting the cyclopentanone intermediate to Luche reduction with NaBH$_4$ in presence of cerium chloride heptahydrate to yield the β-allylic alcohol of formula 15;

wherein the process can be done one-pot or in steps.

The invention also includes novel compounds that are reactants, intermediates or products of the syntheses described herein. In one embodiment, these compounds are selected from the group consisting of:

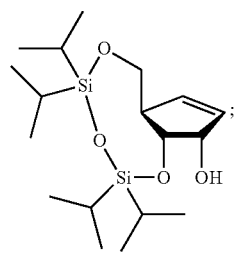
11

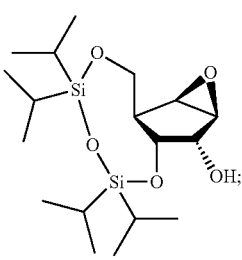
12

-continued

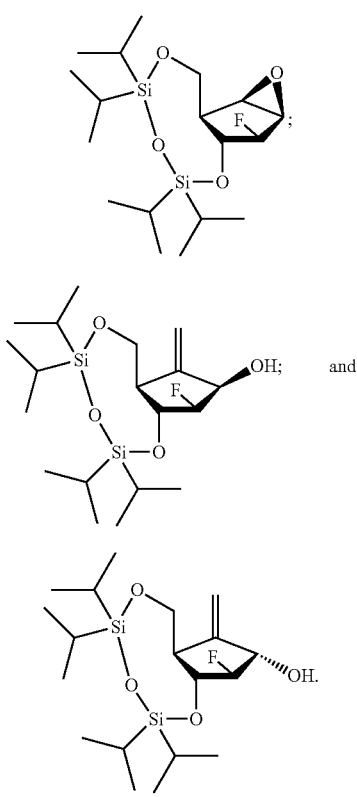

These and other aspects of the invention are described further in the Detailed Description of the Invention.

DETAILED DESCRIPTION OF THE INVENTION

Figure 1:
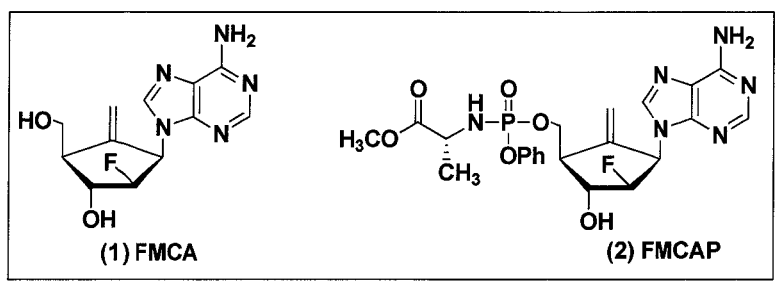
FIG. 1 shows structures of 2'-fluoro-6'-methylene-carbocyclic adenosine (FMCA) and its monophosphate prodrug (FMCAP).

The following terms are used to describe the present invention. In instances where a term is left undefined, the term is given its art recognized meaning. In accordance with the present invention there may be employed conventional chemical synthetic methods and other biological and pharmaceutical techniques within the skill of the art. Such techniques are well-known and are otherwise explained fully in the literature.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described.

It is to be noted that as used herein and in the appended claims, the singular forms "a," "and" and "the" include plural references unless the context clearly dictates otherwise.

The term "compound", as used herein, unless otherwise indicated, refers to any specific chemical compound disclosed herein, generally refers to β-D nucleoside analogs, but may include, within context, tautomers, regioisomers, geometric isomers, anomers, and where applicable, optical isomers (enantiomers) or diastereomers (two chiral centers) thereof of these compounds, as well as pharmaceutically acceptable salts thereof, solvates and/or polymorphs thereof. Within its use in context, the term compound generally refers to a single compound, but also may include other compounds such as stereoisomers, regioisomers and/or optical isomers (including racemic mixtures and/or diastereomers as described herein) as well as specific enantiomers, enantiomerically enriched or individual diastereomers or mixtures of disclosed compounds. It is noted that in the event that a carbon range is provided for a compound, that range signifies that each and every carbon individually is considered part of the range. For example a $C_1$-$C_{20}$ group describes a group with a single carbon, two carbon atoms, three carbon atoms, four carbon atoms, etc. up to twenty carbons.

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids well known in the pharmaceutical art. Sodium and potassium salts are particularly preferred as neutralization salts of the phosphates according to the present invention.

The term "pharmaceutically acceptable derivative" is used throughout the specification to describe any pharmaceutically acceptable prodrug form (such as an ester, ether or amide or other prodrug group) which, upon administration to a patient, provides directly or indirectly the present compound or an active metabolite of the present compound.

The term "alkyl" shall mean within its context a $C_1$-$C_{20}$, preferably a $C_1$-$C_{10}$ linear, branch-chained or cyclic fully saturated hydrocarbon radical, which may be optionally substituted. It is noted that in the event that a carbon range is provided, that range signifies that each and every carbon is considered part of the range. For example a $C_1$-$C_{20}$ group describes a group with a single carbon, two carbon atoms, three carbon atoms, four carbon atoms, etc. The term "ether" shall mean an optionally substituted $C_1$ to $C_{20}$ ether group, formed from an oxygen and an alkyl group, or alternatively, may also contain at least one oxygen within the alkyl or alkylene chain.

The term "aromatic" or "aryl" shall mean within its context a substituted or unsubstituted monovalent carbocyclic aromatic radical having a single ring (e.g., phenyl) or multiple condensed rings (e.g., naphthyl, anthracene, phenanthrene). Other examples include optionally substituted heterocyclic aromatic ring groups ("heteroaromatic" or "heteroaryl") having one or more nitrogen, oxygen, or sulfur atoms in the ring, and preferably include five or six-membered heteroaryl groups, such as imidazole, furyl, pyrrole, furanyl, thiene, thiazole, pyridine, pyrazine, triazole, oxazole, among others, but can also include fused ring heteroaryl groups such as indole groups, among others. The preferred aryl group in compounds according to the present invention is a phenyl or a substituted phenyl group.

The term "heterocycle" shall mean an optionally substituted moiety which is cyclic and contains at least one atom other than a carbon atom, such as a nitrogen, sulfur, oxygen or other atom, which ring may be saturated and/or unsaturated.

The term "unsubstituted" shall mean substituted only with hydrogen atoms. The term "substituted" shall mean, within the chemical context of the compound defined, a substituent (each of which substituent may itself be substituted) selected from a hydrocarbyl (which may be substituted itself, preferably with an optionally substituted alkyl or fluoro group, among others), preferably an alkyl (generally, no greater than about 3 carbon units in length), including $CF_3$, an optionally substituted aryl, halogen (F, Cl, Br, I), thiol, hydroxyl, carboxyl, $C_1$-$C_3$ alkoxy, alkoxycarbonyl, CN, nitro or an optionally substituted amine (e.g. an alkyleneamine or a $C_1$-$C_3$ monoalkyl or dialkyl amine). Various optionally substituted moieties may be substituted with 3 or more substituents, preferably no more than 3 substituents and preferably with 1 or 2 substituents.

The term "acyl" is used throughout the specification to describe a group at the 5' or 3' position of the nucleoside analog (i.e., at the free hydroxyl position in the carbocyclic moiety) or on the exocyclic amine of the nucleoside base which contains a $C_1$ to $C_{20}$ linear, branched or cyclic alkyl chain. The acyl group in combination with the hydroxyl group results in an ester and the acyl group in combination with an exocyclic amine group results in an amide, which, after administration, may be cleaved to produce the free nucleoside form of the present invention. Acyl groups according to the present invention are represented by the structure:

where $R^4$ is a $C_1$ to $C_{20}$ linear, branched or cyclic alkyl group which is optionally substituted preferably with, for example, 1-3 hydroxyl groups, 1-3 halo groups (F, Cl, Br, I) or an amine group (which itself may be optionally substituted with one or two $C_1$-$C_6$ alkyl groups optionally bearing between 1 and 3 hydroxyl groups), alkoxyalkyl (including an ethylene oxide chain which may end in a free hydroxyl group or a $C_1$-$C_{10}$ alkyl group and ranges in molecular weight from about 50 to about 40,000 or about 200 to about 5,000), such as phenoxymethyl, aryl, alkoxy, alkoxycarbonyloxy groups (e.g., [(isopropoxycarbonyl)oxy]-methoxy), aryloxyalkyl, among others, all of which groups may be optionally substituted, as described above. Preferred acyl groups are those where $R^4$ is a $C_1$ to $C_{12}$ alkyl group. Acyl groups according to the present invention also include, for example, those acyl groups derived from benzoic acid and related acids, 3-chlorobenzoic acid, succinic, capric and caproic, lauric, myristic, palmitic, stearic and oleic groups, among numerous others and may include such related groups as sulfone groups such as mesylate groups. All groups may be appropriately substituted within context as otherwise described herein. One of ordinary skill in the art will recognize the acyl groups which will have utility in the present invention, either to synthesize the target pharmaceutical compounds or as prodrug of the nucleosides according to the present invention.

The term "amino acid" or "amino acid residue" shall mean, within context, a radical of a D- or L-amino acid which is covalently bound to a nucleoside analog at the 4' exocyclic amine position of the cytosine base or the 5'- or 3'-OH position of the sugar synthon ($R^2$, $R^1$ or $R^{1a}$) through a carboxylic acid moiety of the amino acid, thus forming respectively, an amide or ester group linking the nucleoside to the amino acid. Amino acids may also be used to provide phosphoamidate groups in nucleoside compounds according to the present invention as otherwise described herein. Representative amino acids include both natural and unnatural amino acids, preferably including, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine, among others.

The term "phosphate ester" or "phosphodiester" (which term includes phosphotriester groups and phosphoamidate groups in context) is used throughout the specification to describe mono-phosphate groups at the 5' position of the carboyclic sugar synthon which are mono- or diesterified (or amidated and optionally esterified in the case of a phosphoamidate) such that the phosphate group is negatively charged or is rendered neutral, i.e., has a neutral charge. Phosphate esters, phosphodiesters and/or phosphoamidate groups for use in the present invention include those represented by the structures:

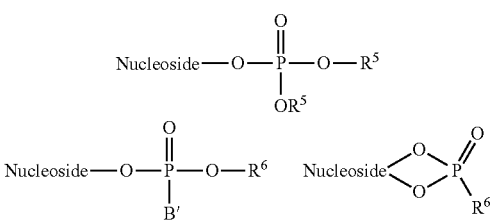

where each $R^5$ and $R^6$ is independently selected from H, a $C_1$ to $C_{20}$ linear, branched or cyclic alkyl group, alkoxyalkyl, aryloxyalkyl, such as phenoxymethyl, optionally substituted aryl (especially an optionally substituted phenyl group) and alkoxy, among others, including alkoxycarbonyloxy groups (e.g., (isopropoxycarbonyl)oxy]-methoxy) each of which groups may be optionally substituted (e.g., a phenyl or other group may be optionally substituted as otherwise described herein or preferably with from one to three, $C_1$-$C_6$ alkyl groups, halogen, preferably F, Cl or Br, nitro, cyano, or $C_2$-$C_6$ carboxyester groups) with the proviso that at least one $R^5$ group is other than H, or the two $R^5$ groups together form a five- or six-membered heterocyclic group;

B' is a

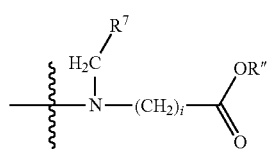

group or a group obtained from an amino acid (a natural or unnatural amino acid such as, for example, alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine, among others) to preferably provide a group according to the structure

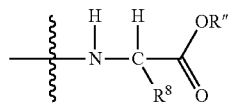

where i is 0, 1, 2 or 3 (preferably 0)

$R^7$ is a $C_1$ to $C_{20}$ linear, branched or cyclic alkyl or acyl group, alkoxyalkyl, aryloxyalkyl, such as phenoxymethyl, optionally substituted aryl group (as described above) and alkoxy, among others, each of which groups may be optionally substituted;

$R^8$ is sidechain of an amino acid, preferably a sidechain of an amino acid selected from the group consisting of alanine, β-alanine, arginine, asparagine, aspartic acid, cysteine, cystine, glutamic acid, glutamine, glycine, phenylalanine, histidine, isoleucine, lysine, leucine, methionine, proline, serine, threonine, valine, tryptophan or tyrosine (preferably $R^8$ is derived from alanine, leucine, isoleucine or threonine, more preferably alanine-$R^8$ is methyl), and R" is a $C_1$ to $C_{20}$ linear, branched or cyclic alkyl or a phenyl or heteroaryl group, each of which groups is optionally substituted.

Preferred monophosphate esters for use in prodrug forms according to the present invention are those where $R^5$ is a $C_1$ to $C_{20}$ linear or branched chain alkyl group, more preferably a $C_1$ to $C_3$ alkyl group, all of which groups may be optionally substituted. Other compounds which are preferred are as otherwise set forth herein, especially, where $R^1$ is a phosphoamidate group as otherwise described herein. A preferred phosphoamidate is

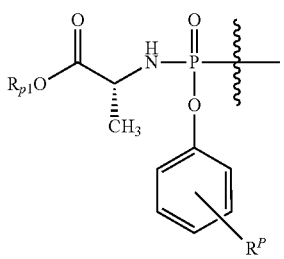

where $R_{p1}$ is an optionally substituted (OH, halo) $C_1$-$C_{20}$ alkyl group, preferably a $C_1$-$C_4$ alkyl group, even more preferably a methyl, ethyl, isopropyl group or isobutyl group; and $R^P$ is H, nitro, cyano, methoxy, or a $C_1$-$C_3$ alkyl group optionally substituted with from 1-3 halogen substituents (preferably F).

Preferred phosphoamidate groups for $R^1$ include those according to the chemical structure:

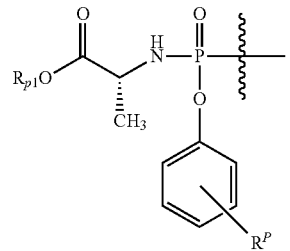

where $R^P$ is H or $C_1$-$C_3$ alkyl group (preferably H) and $R_{p1}$ is methyl, ethyl, isopropyl or isobutyl group, more preferably a methyl or isopropyl group.

In other embodiments $R^1$ is a

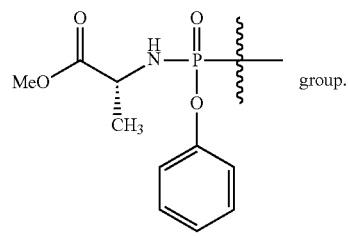 [SMILES: *P(=O)(N[C@H](C)C(=O)OC)Oc1ccccc1 ; "group."]

group.

The term "effective amount" shall mean an amount or concentration of a compound according to the present invention which is effective within the context of its administration or use, which may be inhibitory, prophylactic and/or therapeutic. Within context, all active compounds which are used in the present invention are used in effective amounts. The present compound also relates to combinations of compounds which contain effective amounts of each of the compounds used, whether that combination is additive or synergistic in effect, provided that the overall effect of the combination of compounds is to inhibit the growth, reduce the likelihood of or treat viral infections in patients as otherwise described herein.

The term "D-configuration" as used in the context of the present invention refers to the configuration of the nucleoside compounds according to the present invention which mimics the natural configuration of sugar moieties as opposed to the unnatural occurring nucleosides or "L" configuration. The term "β" or "β anomer" is used to describe nucleoside analogs according to the present invention in which the nucleoside base is configured (disposed) above the plane of the carbocyclic moiety in the compound.

The term "enantiomerically enriched" is used throughout the specification to describe a nucleoside which includes at least about 95%, preferably at least about 96%, more preferably at least about 97%, even more preferably, at least about 98%, and even more preferably at least about 100% or more of a single enantiomer of that nucleoside. Carbocyclic nucleoside compounds according to the present invention are generally β-D-nucleoside compounds. When the present compounds according to the present invention are referred to in this specification, it is presumed that the nucleosides have the D-nucleoside configuration and are enantiomerically enriched (preferably, about 100% of the D-nucleoside), unless otherwise stated. The term "diastereomerically pure" is used to describe a single diastereomer of a compound according to the present invention which contains at least 95%, 96%, 97%, 98%, 99%, 99.5% or 100% by weight of a single diastereomer to the exclusion of other possible diastereomers.

An Improved Synthetic Methodology Amenable for Large Scale Production of D-2'-fluoro-6'-methylene cyclopentenol (15)

For a new methodology, the major problem was to generate the enantiomerically pure carbocyclic intermediate 15 in a shorter step with fixed stereogenic center via milder reactions, with cost effective method that can be amenable for a large scale synthesis. Therefore, herein we report the full account of significantly improved synthetic methodology amenable for a large scale of D-2'-fluoro-6'-methylene cyclopentenol (15) in comparison to the previously reported method.[6] The newly developed methodology may also be utilized in the synthesis of other carbocylic nucleosides of therapeutic interest.

Results and Discussion

The retrosynthetic analysis of FMCA is illustrated in Scheme 1. The strategy was to synthesize the key chiral intermediate, 2'-β-fluoro-6'-methylene-cyclopentanol (15), from (1S)-(±)-2-azabicyclo[2.2.1]hept-5-en-3-one (3), commonly known as, Vince lactam. The lactam was first introduced by Robert Vince which has been used as a synthetic intermediate for various carbocyclic nucleosides, including puromycin,[12] carbovir[13] and abacavir[14].

To explore the path A, we tried several oxidative methods for the conversion of amine 8 to a ketone analog 19, including $KMnO_4$, $CrO_4$, the Corey's oxidation of amine to ketone[15], however, in every case it was unsuccessful. The failure of this crucial conversion led us to the path B. Diazotization of the anime followed by an elimination reaction would produce the alkene 9. Stereoselective epoxidation followed by fluorination of 9 would give 13. Selective opening of the epoxide would construct the key intermediate 15 for the synthesis of FMCA.

only the optically pure (−) lactam 5 in 84% yield with an enantiomeric excess (ee) of more than 99%. It has been reported that the stereochemistry of $OsO_4$ catalyzed hydroxylation of (−)-2-azabicyclo[2.2.1]hept-5-en-3-one (γ-lactam 3) can be controlled through the N—H protecting group of the lactam.[17,18] Sterically a large group directs the hydroxylation to the exo-face of an olefin, yielding a hydroxylation product that can be converted into an analogue of carbocyclic riboside as the exo-isomer was desired for our synthesis. Thus, a bulkier boc-protecting group would prevent the $OsO_4$ oxidation from the β-face of the olefin and favors the production of the α-diol. Catalytic cis-hydroxylation of 5 was then carried out with $OsO_4$ and 4-methylmorpholine N-oxide (NMO) in $H_2O$/acetone/tert-butyl alcohol for 4 hours at room temperature afforded a complete conversion of 5 to a single product 6 in 70% yield. Benzoylation of 6 was performed with benzoyl chloride and DMAP in DCM at 0° C. to room temperature gave the benzoyl protected lactam. Opening of the lactam was accomplished by treating with sodium borohydride ($NaBH_4$) in methanol to provide the alcohol 7 in 83% yield. Deprotection of the HN-Boc group was carried out by using 2M solution of HCl/ether in THF for 16 hours at room temperature to give the amine 8 in 90% yield.

With the benzoyl protected amine 8 in hand, our first approach was to oxidize the amine to a ketone that would directly convert to a cyclopentanone 19 (Scheme-1). In our case, the reaction did not proceed satisfactorily. Only 5% the ketone was formed by the Corey's oxidation method[15]. Therefore, we devised an alternative approach to convert the amine 8 to the alkene 9 via the diazotization-elimination reaction. The amine 8 was treated with sodium nitrite ($NaNO_2$) in a 50% acetic acid/water mixture for diazotization in acetonitrile, followed by elimination of the diazonium salt in situ at 0° C. to room temperature to give the alkene 9 in 54% yield. To improve this step, a number of variations for the Scheme-1 Retro Synthetic Analysis of FMCA.

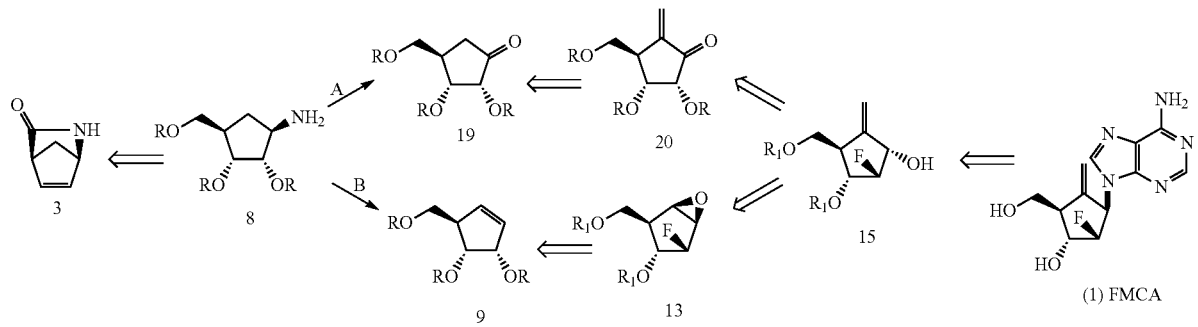

Optically pure γ-lactam (−)-(1R,4S)-tert-butyl-3-oxo-2-azabicyclo[2.2.1]hept-5-ene-2-carboxylate (5) was synthesized by the reported procedure.[16] On treatment of commercially available γ-lactam (±) 3 with di-tert-butyl dicarbonate in the presence of a catalytic amount of 4-dimethylaminopyridine (DMAP) in THF afforded N-Boc protected (±) γ-lactam 4 in 80% yield (Scheme 2). The resolution of the (±) γ-lactam 4 was carried out with savinase in 50% THF-phosphate buffer solution (pH 8.0) for 2 days selectively produces diazotization reaction including, different organic acids, HCl, $HClO_4$, $H_2SO_4$ etc, were tried; however, no any significant improvement of the yield was obtained. In another attempt by a sequential N,N-dimethylation reaction with formalin-sodium cyanoborohydride, m-CPBA oxidation to N-oxide, and then thermal cope elimination[19] in THF gave only 48% of yield. The debenzoylation of 9 was carried out by sodium methoxide (NaOMe) in methanol to give the triol 10 in 82% yield.

Scheme 2 Synthesis of FMCA 1 from Vince Lactam 3

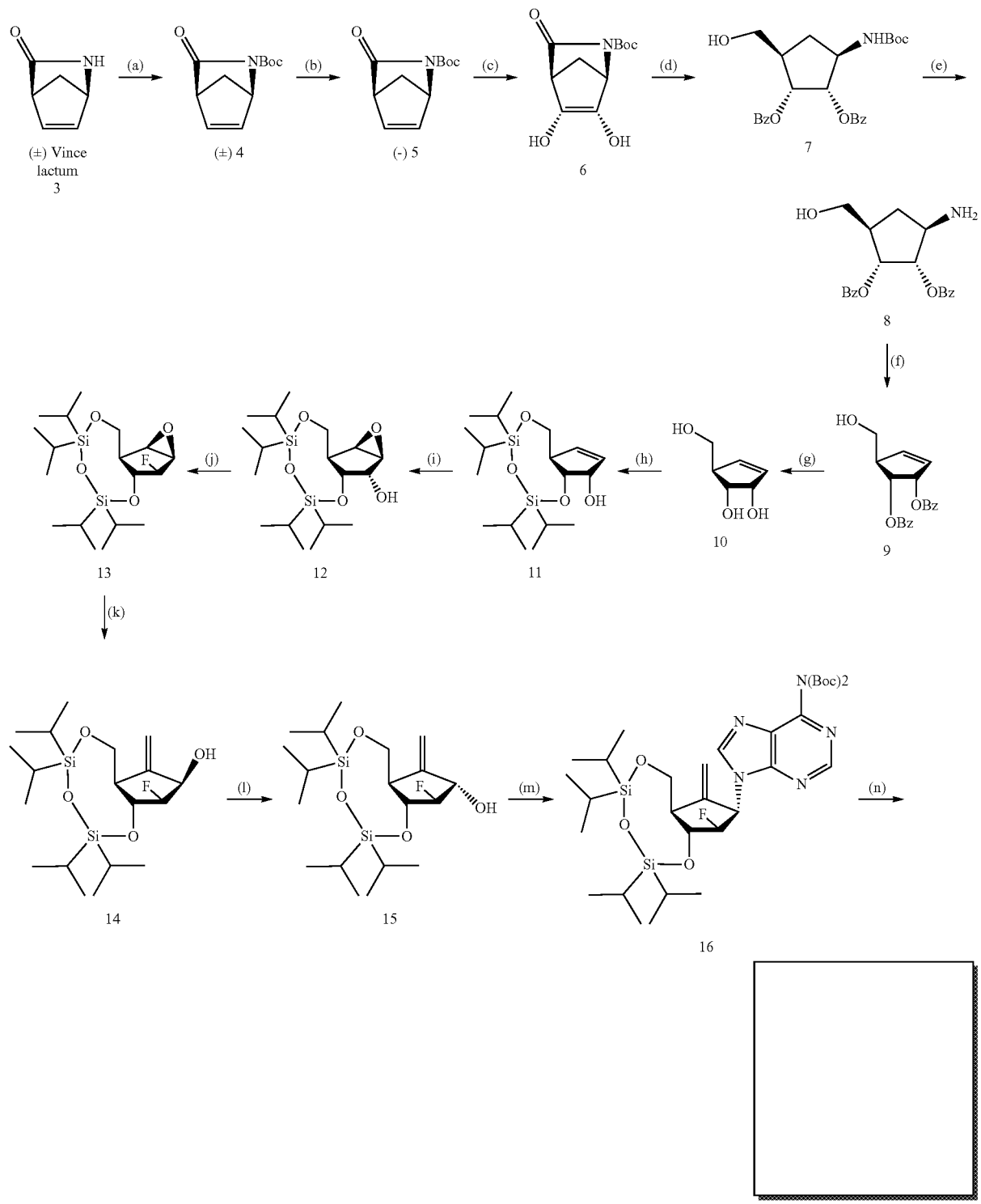

Reagents and Conditions: (a) (Boc)₂O, DMAP, THF; (b) Savinase, THF, Buffer solution; (c) OsO₄, NMO, Acetone; (d) i) BzCl, Pyridine; ii) NaBH₄, Methanol; (e) HCl/Ether, Methanol; (f) NaNO₂, Acetic Acid, Water, Acetonitrile; (g) NaOMe, Methanol; (h) TIDPSCl₂, Imidazole, DCM; (i) m-CPBA, DCM; (j) DAST, DCM; (k) n-BuLi, trimethylsulfonium iodide, THF; (l) i) Dess-martin periodinane, DCM; ii) NaBH₄, CeCl₃.7H₂O, Methanol; (m) Boc-Adnine, DIAD, TPP, THF; (n) TFA, TBAF/THF.

Our next crucial step was to introduce a fluorine at 2-position in the carbocyclic moiety (compound 12). Previously, diethylaminosulfur trifluoride (DAST) fluorination of α/β epoxide with a cis/trans hydroxyl group was studied by P. Lakshmipathi et al.[20] in which they reported that the cis (α)-epoxide with a hydroxyl group with DAST obtained a cyclic ring-expanded product rather than the desired fluorinated compound. On the other hand, the trans (β)-epoxide with respect to a hydroxyl group gave the expected fluorinated epoxide in excellent yield. These results encouraged us to prepare the trans (β)-epoxide 12 from the allyl alcohol 11, to obtain the fluoro epoxide 13.

To accomplish these reactions, first we attempted the epoxidation on the olefin 10 with m-CPBA (77%) in 20% methanol/water, which exclusively resulted in the undesired cis (α)-epoxide in 85% yield. Thus, in order to obtain the opposite trans (β)-epoxide, silylation of 3',5' hydroxyl groups were first carried out using 1,3-dichloro-1,1,3,3-tetraisopropyldisiloxane (TIDPSCl$_2$)/imidazole in DMF to give the 3',5'-silyl protected alcohol 11 in 82% yield. The epoxidation of 11 with m-CPBA in DCM selectively gave the desired trans β-epoxide 12 in 85% yield. The epoxidation by m-CPBA was probably prevented by the bulkier silyl protecting group from the α-face, resulting in the trans β-epoxide. The stereochemistry of the α- and β-epoxide was confirmed by 1H-1H rotating-frame nuclear overhauser effect correlation spectroscopy (ROESY). Conversion of the trans β-epoxide 12 to cis-fluoro β-epoxide 13 was accomplished by treating 12 with DAST at −20° C. for 1 hour furnished cis-fluoro β-epoxide 13 in 54% yield. It was observed that the fluorination with DAST was temperature sensitive; at higher temperature (>−10° C.) the formation of a variety of side products were observed on TLC. The reaction was quenched with ice at low temperature (<−10° C.) because quenching at >0° C. decreases the yield of the desired product 13.

The addition of a 6'-methylene group on the cyclopentyl ring was accomplished by a regioselective ring opening reaction of the epoxide 13 reported by Alcaraz L. et al[21] to produce the allylic alcohol 14 with retention of the β-configuration; the β-epoxide 13 was treated with dimethylsulfonium methylide at −10° C. to afford the β-allylic alcohol 14 in 81% yield. It was found that the addition of exocyclic double bond via an epoxide ring opening reaction was more convenient than our previously reported method.[11] The confirmation of the β-allylic alcohol 14 was validated by the 1H NMR and 1H-1H ROESY spectroscopy; The 1H NMR spectrum of compound 14 revealed distinct multiplicities due to H—F coupling: a double triplet of H-2 at δ 4.73 (H-2), a multiplet of anomeric H-1 proton at δ 4.48 (H-1), a multiplet at δ 4.44 (H-3) and a multiplet at δ 2.58 (H-4). The 1H-1H ROESY spectra of 14 showed the correlation among the proton H-4 with the anomeric H-1 proton as well as with H-2 proton (FIG. 2), which confirmed that these protons have the same orientation, indicating the β-configuration of the OH group in 14.

Figure 2:
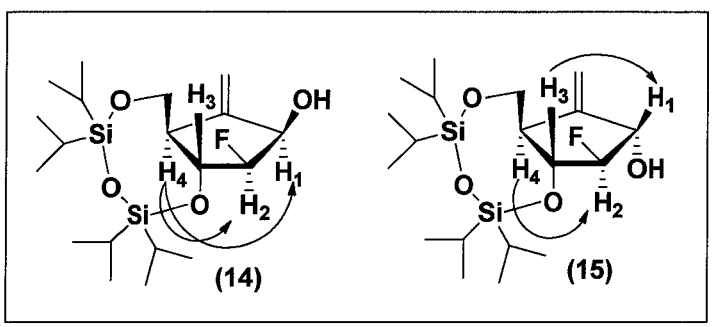
FIG. 2 shows 1H-1H ROESY correlations of compound 14 and 15.

In order to condense the carbocyclic moiety with adenine to synthesize the desired nucleoside, an inversion of configuration of 14 was required for which Mitsunobu reaction[21] was first tried; coupling of benzoic acid in the presence of diisopropyl azodicarboxylate (DIAD) and triphenylphosphine (TPP) prepared α-benzoic ester of 14 via SN$^2$ mechanism, which upon hydrolysis usually produces an α-alcohol. However, during the hydrolysis of ester it was found that elimination of the fluorine was observed from compound 15, which was confirmed by $^{19}$F-NMR spectroscopy. Thus, it was concluded that the basic condition was not suitable for 14. We searched for an alternative inversion method, for which oxidation of 14 with the Dess-martin periodinane reagent at 0° C. gave the cyclopentanone intermediate in 90% yield. Upon Luche reduction[22] with NaBH$_4$ in presence of cerium chloride heptahydrate (CeCl$_3$.7H$_2$O) at −78° C. to 0° C. selectively gave a single preferred a isomer 15 in 86% yield. The anomeric H-1' of compound 15 exhibited doublets of doublet at δ 4.47 (H-1), double triplet at δ 4.65 (H-2) due to H—F coupling, multiplet at δ 4.23 (H-3) and multiplet of H-4 at δ 2.66 ppm in 1H-NMR spectrum. In 1H-1H ROESY analysis of 15, H-4 shows correlation with the 11-2, not with the anomeric proton H-1, while H-3 shows correlation with H-1 proton confirmed the α configuration of the alcohol 15 (FIG. 2).

Compound 15 served as the key intermediate for synthesis of FMCA. Coupling of 15 with Boc-protected adenine was accomplished under Mitsunobu coupling conditions using diisopropyl azodicarboxylate (DIAD) and triphenylphosphine (TPP) in THF to produced 16 in 65% yield. To increase the yield of this coupling reaction, various methods were tried; converting the hydroxyl group of 14 to α-bromo cyclopentane 17 by treatment of 14 with carbon tetra bromide (CBr$_4$) with TPP in DCM at 0° C. furnished 86% of the α-bromo compound 17 through the SN$^2$ mechanism (Scheme 3). The α-bromo compound 17 was reacted with the anion of Boc-protected adenine generated by K$_2$CO$_3$ in DMF to obtain the compound 16. From the reaction we obtained an addition product 18 in 80% of yield, instead of SN$_2$ product (FMCA analog, 16) as the adenine anion attacked the terminal-methylene carbon of the cyclopentane ring of 17 rather than the (pseudo) anomeric carbon (C1). Consequently, we found the Mitsunobu coupling reaction is the better method to produce compound 16 in the adequate yield. Boc and silyl protecting group of 16 was removed by using tetrabutylammonium fluoride (TBAF, 1M solution in THF)/trifluoroacetic acid (TFA) in THF at room temperature afforded the targeted compound 1 (FMCA) in 85% yield.

Scheme 3 Addition-elimination reaction instead of SN$^2$ reaction

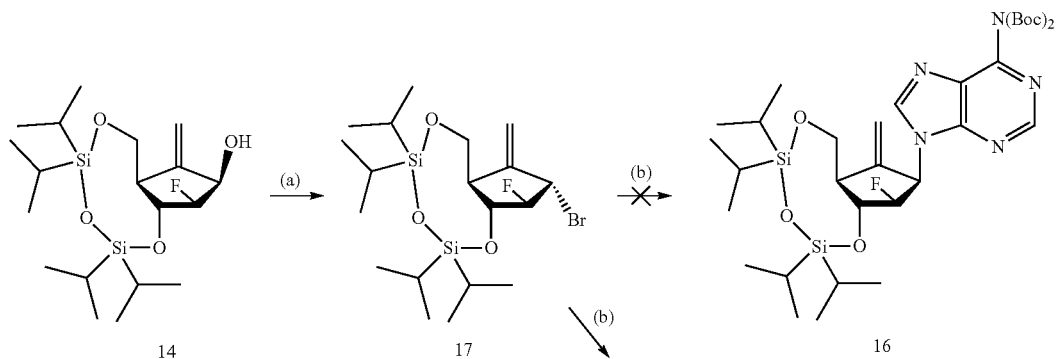

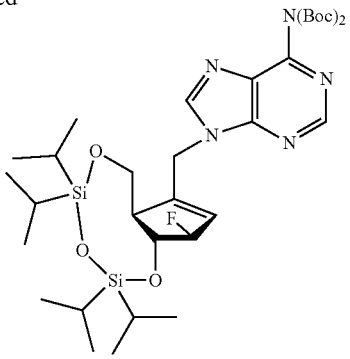

18

Reagents and Conditions: (a) CBr$_4$, TPP, DCM; (b) K$_2$CO$_3$, 15-crown ether, DMF.

Conclusion

In summary, we have developed an efficient practical synthetic method for the key carbocyclic intermediate 15 in a multi-gram scale from Vince lactam via kinetic resolution of the lactam 5, diazotization/elimination of the amine derivative 8, stereoselective epoxidation of 11, regioselective fluorination of 12, epoxide opening-introduction of olefin of 13, inversion of the OH group of 14, followed by the condensation of the key intermediate 15 completed the synthesis of the final nucleoside (FMCA). It is expected that the new synthetic method may be suitable for the preparation of a large scale amount of FMCA for preclinical studies.

Experimental Section

General Analytical Methods.

Melting points were determined on a Mel-temp II laboratory device and are uncorrected. Nuclear magnetic spectra were recorded on Varian Mercury 400 spectrometer at 400 MHz for $^1$H NMR and 100 MHz for $^{13}$C NMR or Varian Inova 500 spectrometer at 500 MHz for $^1$H NMR and 125 MHz for $^{13}$C NMR with tetramethylsilane as an internal standard. Chemical shifts (δ) are quoted as s (singlet), bs (broad singlet), d (doublet), t (triplet), q (quartet), m (multiplet), dd (double doublet), dt (double triplet). U.V spectra were recorded on a Beckman DU-650 spectrophotometer. Optical rotations were measured on JASCO DIP-370 digital polarimeter. High resolution mass spectra were recorded on a Micromass Autospec high-resolution mass spectrometer. Elemental analyses were performed by Atlantic Microlabs Inc. Norcross, Ga. TLC was performed on Uniplates (Silica Gel) purchased from Analtech Co.

(±)-tert-Butyl 3-oxo-2-azabicyclo[2.2.1]hept-5-ene-2-carboxylate (4)

A solution of di-tert-butyl dicarbonate (500 g, 2.291 mol) in tetrahydrofuran (200 ml) was added slowly to a suspension of racemic 3 (250.0 g, 2.291 mol), and 4-dimethylaminopyridine (2.8 g, 22.91 mmol) in tetrahydrofuran (2000 ml). The brown turbid solution was stirred at 20° C. until the reaction was completed. The solution was concentrated in vacuo to give brown foam. Recrystallization twice from cyclohexane afforded the product 4 (racemic) as pale pink crystals (384 g, 80%); mp 70.5-71.5° C.; NMR (CDCl$_3$): δ 1.5 (s, 9H), 2.15 (d, J=8.5 Hz, 1H), 2.35 (d, J=8.5 Hz, 1H), 3.39 (s, 1H), 4.96 (s, 1H), 6.66 (m, 1H), 6.89 (dd, J=5.6 & 2.1 Hz, 1H); MS: (M+H)$^+$ 210.

(−)-[(1R,4S)-tert-Butyl 3-oxo-2-azabicyclo(2.2.1)hept-5-ene-2-carboxylate] (5)

Savinase (500 ml, 16 U/g) was added to a solution (3000 ml) containing (335 g 1.6 mol) racemic (±) 2 in 50% tetrahydrofuran/50% phosphate buffer (50 mM, pH 8.0) at 30° C. The reaction was stirred at room temperature for 2 days. Upon completion of the reaction, the pH of the reaction mixture was raised to pH 9.0 with a saturated solution of sodium bicarbonate. The mixture was then extracted with cyclohexane (500 mL×3). The combined organic layer was washed with 700 ml of sodium a bicarbonate solution and subsequently washed with 500 ml of brine. Evaporation and drying yielded a brown crude, which was purified by silica gel column chromatography (20% EtOAc/hexane) gave an optically pure white solid (−)-5 (140 g, 84%). The lactam was identified by 1H NMR as well as in comparison to an authentic sample $[\alpha]^{24}_D$ −194°, c 2.0, CHCl$_3$). The enantiomeric excess (ee) was better than 99% as analyzed by the optical rotation; $[\alpha]^{24}_D$ −193° (c 2.0, CHCl$_3$); Mp 88.6° C.; NMR (CDCl$_3$): δ 1.5 (s, 9H), 2.15 (d, J=8.5 Hz, 1H), 2.35 (d, J=8.5 Hz, 1H), 3.39 (s, 1H), 4.96 (s, 1H), 6.66 (m, 1H), 6.89 (dd, J=5.6 & 2.1 Hz 1H).

(−)-(1R,4S,5R,6S)-tert-Butyl5,6-dihydroxy-3-oxo-2-azabicyclo[2.2.1]heptane-2-carbo-late (6)

To a solution of tert-butyl 3-oxo-2-azabicyclo(2.2.1)hept-5-ene-2-carboxylate 5 (50.0 g, 239.2 mmol) in acetone (200 mL), 4-Methylmorpholine N-oxide (55.9 g, 477.7 mmol) was added at 0° C. while stirring, followed by adding a solution of OsO$_4$ (121 mg, 0.476 mmol) in tert-butyl alcohol (2.5 mL), and the mixture was stirred at room temperature for 2 h. Solvent was evaporated in vacuo, and the residue was purified by flash column chromatography on silica gel using 30% EtOAc/hexane as the eluent to give a white solid of 6 (41 g, 70%). $[\alpha]^D_{24}$ −28.19 (c 1.0 CHCl$_3$); $^1$H-NMR (500 MHz, CDCl$_3$): 1.52 (s, 9H), 1.99 (d, J=10.5 Hz, 1H), 2.10 (d, J=10.5 Hz, 1H), 2.80 (m, 1H), 3.76 (bs, 1H), 3.92 (bs, 1H), 4.09 (m, 1H), 4.24 (m, 1H), δ 4.33 (m, 1H); HR-MS Calcd. For (C$_{11}$H$_{17}$NO$_5$+H)$^+$ 244.1107. found 244.1321.

(−)-(1R,2S,3R,5R)-3-(tert-Butoxycarbonyl)amino)-5-(hydroxymethyl)cyclopentane-1,2-diyl dibenzoate (7)

Benzoyl chloride (45.8 mL, 395 mmol) was added to a solution of diol 6 (40 g, 164.4 mmol) and DMAP (40.2 g, 329 mmol) in anhydrous dichloromethane (500 ml) at 0° C. The mixture was then stirred for 1 h, quenched with water and extracted with DCM (500 mL×2). The combined organic layer was washed with brine (250 mL) and dried over $Na_2SO_4$. The solvent was removed and the residue was purified by silica gel column chromatography (8% EtOAc/hexane) to give benzoylated intermediate as a white solid. $[\alpha]^{24}_D$ −43.40; $^1$H-NMR (500 MHz, $CDCl_3$): δ 1.57 (s, 9H), 2.76 (d, J=10.5 Hz, 1H), 2.43 (d, J=10.5 Hz, 1H), 3.13 (m, 1H), 4.70 (m, 1H), 5.48 (d, J=5.5 Hz, 1H), 5.59 (d, J=5.5 Hz, 1H), 7.25 (m, 4H), 7.50 (m, 2H), 7.82 (m, 4H). To the benzoylated intermediate (63.8 g, 141 mmol) dissolved in Methanol (500 ml) sodium borohydride (11.76 g, 311 mmol) was added at 0° C. The reaction mixture was allowed to warm to room temperature, and after 1.5 h, the mixture was quenched with 1 N HCl and concentrated in vacuo. The aqueous layer was extracted with ethyl acetate (500 mL×2) and combine organic layer was washed with water, dried over $Na_2SO_4$ and concentrated in reduced pressure. The residue was purified by silica gel column chromatography (50% DCM/hexane) to give compound 7 (53.4 g, 83%) as a white solid. mp 78-79° C.; $^1$H-NMR (500 MHz, $CDCl_3$): δ 1.43 (s, 9H), 2.52 (m, 2H), 3.72 (m, 1H), 3.87 (m, 1H), 4.52 (m, 1H), 5.30 (m, 1H), 5.38 (s, 1H), 5.56 (m, 1H), 7.38 (m, 4H), 7.54 (m, 2H), 7.97 (m, 4H); HR-MS Calcd. For $(C_{25}H_{29}NO_7+H)^+$ 456.1944. found 456.2017.

(−)-(1R,2S,3R,5R)-3-Amino-5-(hydroxymethyl) cyclopentane-1,2-diyldibenzoate hydrochloride (8)

2 M solution of HCl in ether (121 ml) was added in stirring solution of compound 7 (55.0 g, 121 mmol) in methanol at 0° C. The mixture was allowed to warm to room temperature gradually and stirring continued for 8 h. Solvent was evaporated under reduced pressure, and the residue was treated with anhydrous ether (120 mL) to precipitate the product 8. The precipitated product was washed with ether (50 mL×2) afforded hydro chloride salt of amine 8 as white solid (42.0 g, 90%). $[\alpha]^{25}_D$ −28.19° (c 1.0, MeOH); $^1$H NMR (500 MHz, DMSO-$d_6$): δ 1.63 (m, 1H), 2.39 (m, 1H), 2.46 (m, 1H), 3.52 (m, 1H), 3.61 (m, 1H), 3.96 (m, 1H), 5.07 (m, 1H), 5.48 (m, 2H), 7.45 (m, 4H), 7.64 (m, 2H), 7.88 (m, 4H), 8.40 (bs, 2H, $D_2O$ exchange, $NH_2$); $^{13}$C NMR (125 MHz, DMSO-$d_6$) δ 27.7, 43.7, 53.0, 61.5, 73.5, 75.1, 128.9, 129.0, 129.1, 129.4, 129.6, 129.8, 134.0, 165.3, 227.7; HR-MS Calcd. For $(C_{20}H_{21}NO_5)^+$ 355.1420. found 355.1293.

(+)-(1R,2S,5R)-5-(Hydroxymethyl)cyclopent-3-ene-1,2-diyl dibenzoate (9)

To a well stirred solution of (−)-(1R,2S,3R,5R)-3-amino-5-(hydroxymethyl)cyclopentane-1,2-diyl dibenzoate hydrochloride (8) (42.0 g, 107.0 mmol) in a mixture of acetonitrile/water (1:1) sodium nitrite (16.27 g, 236.0 mmol) was added portion wise at 0° C. After 15 minutes, 50% aqueous acetic acid was added drop wise over a period of 0.5 h and the mixture was then vigorously stirred for 2 h. The organic solvent was removed under reduced pressure and rest of mixture was quenched with water. The aqueous phase was extracted with ethyl acetate (100 mL×3). The combined organic layer was dried over $Na_2SO_4$, filtered and solvent was removed under reduced pressure. The residue was purified by flash silica gel column chromatography (20% EtOAc/hexane) to give compound 9 (21.5 g, 54%). $[\alpha]^{24}_D$ −156° (c 1.0, $CHCl_3$); $^1$H NMR (500 MHz, $CDCl_3$): δ 2.29 (m, 1H), 3.27 (m, 1H), 3.87-3.82 (m, 1H), 5.54 (m, 1H), 6.11 (m, 1H), 7.28 (m, 2H), 7.38 (m, 2H), 7.52 (m, 2H), 7.89 (m, 2H), 8.05 (m, 2H); $^{13}$C NMR (125 MHz, $CDCl_3$) δ 53.1, 63.0, 74.1, 128.2, 128.3, 129.5, 129.7, 129.9, 133.0, 133.2, 136.9, 150.0, 165.9, 166.6, 185.4; HR-MS Calcd. For $(C_{25}H_{29}NO_7+H)^+$ 339.1154. found 339.1286.

(+)-(1R,2S,5R)-5-(Hydroxymethyl)cyclopent-3-ene-1,2-diol (10)

To a stirred solution of (1R,2S,5R)-5-(hydroxymethyl)cyclopent-3-ene-1,2-diyl dibenzoate (9) (19.2 g, 56.7 mmol) in methanol at room temperature under nitrogen atmosphere sodium methoxide (25 wt % in methanol) (38.9 mL, 170 mmol) was added drop wise over a period of 20 minutes. The mixture was stirred at room temperature for 2 h and quenched by drop wise addition of 1N HCl solution to neutral pH. The solvent was removed under reduced pressure and the residue was purified by silica gel column chromatography (5% Methanol/DCM) to give triol 10 (6.1 g, 84%) as an oil; $[\alpha]^{24}_D$ +254.04° (c 1.0, MeOH); $^1$H NMR (500 MHz, $CD_3OD$) δ 2.78 (d, J=5.0 Hz, 1H), 3.73 (dd, J=5.0, 11.0 Hz, 1H), 3.55 (dd, J=6.5, 10.5 Hz, 1H), 3.93 (t, 1H), 4.50 (t, 1H), 5.88-5.87 (m, 1H), 5.97 (d, J=6.0 Hz, 1H); $^{13}$C NMR (125 MHz, $CD_3OD$) δ 53.7, 62.2, 73.2, 74.5, 132.0, 135.0; HR-MS Calcd. For $(C_6H_{10}O_3-H)^+$ 129.0630. found 129.0553.

(+)-(6aR,9S,9aR)-2,2,4,4-Tetraisopropyl-6,6a,9,9a-tetrahydrocyclopenta[f][1,3,5,2,4]trioxad-isilocin-9-ol (11)

To a stirred mixture of triol 10 (5.8 g, 44.6 mmol) and imidazole (21.2 g, 312.3 mmol) in DMF (300 mL), 1,3-dichloro-1,1,3,3-tetraisopropyldisiloxane (14.7 mL, 46.8 mmol) was added drop wise at 0° C. under nitrogen. The mixture was stirred at room temperature for 2.5 h, quenched with water (200 mL) and extracted with ethyl acetate (3×200 ml). The combined organic layer was washed with brine (2×100 ml), followed by with water and dried over $Na_2SO_4$. The solvent was removed under reduced pressure and the residue was purified by silica gel column chromatography (EtOAc: Hexane 1:30 to 1:5) to give 11 (13.7 g, 82%) as an oil. $[\alpha]^{24}_D$ +45.87° (c 1.0, $CHCl_3$); $^1$H NMR (500 MHz, $CDCl_3$) δ 0.93-1.04 (m, 28H), 2.90 (m, 1H), 3.16 (d, J=2.0 Hz, 1H), 3.51 (m, 1H), 4.01 (dd, J=3.0, 11.0 Hz, 1H), 4.21 (t, 5.6 Hz, 1H), 4.47-4.45 (m, 1H), 5.60 (dd, J=1.5, 6.0 Hz, 1H), 5.86 (dd, J=3.0, 6.5 Hz, 1H); $^{13}$C NMR (125 MHz, $CDCl_3$) δ 12.6, 12.7, 12.9, 13.2, 13.3, 13.4, 17.0, 17.1, 17.2, 17.3, 17.4, 17.6, 54.6, 66.7, 74.7, 76.3, 132.5, 134.4; HR-MS Calcd. For $(C_{18}H_{36}O_4Si_2+Na)^+$ 395.2152. found 395.2052.

(+)-(6aS,6bR,7aS,8aR)-2,2,4,4-Tetraisopropylhexahydrooxireno[2',3':3,4]cyclopenta[1,2-f][1,3,5,2,4]trioxadisilocin-8-ol (12)

To a stirred solution of compound 11 (13.7 g, 36.8 mmol) in dichloromethane (300 mL), m-CPBA (15.9 g, 92.0 mmol) was added portion wise at room temperature. The mixture was stirred at room temperature for 16 h, quenched with a saturated $NaHCO_3$ solution and extracted with DCM (200 mL×2). The combined organic layer was washed with brine (100 mL×2) and dried over $Na_2SO_4$. The solvent was removed under reduced pressure and residue was purified by silica gel column chromatography (3% EtOAc/Hexane) to give epoxide 12 (12.2 g, 85%) as an oil. $[\alpha]^{24}_D$ +18.25° (c 1.0, $CHCl_3$); $^1$H NMR (500 MHz, $CDCl_3$) δ 1.00-1.11 (m, 28H), 2.30 (in, 1H,), 3.05 (s, 1H), 3.37 (s, 1H), 3.56 (d, J=2.5 Hz, 1H), 3.99-4.05 (m, 2H), 4.19 (d, J=5.0 Hz, 1H), 4.26 (dd, J=3.0, 11.5 Hz, 1H); $^{13}$C NMR (125 MHz, $CDCl_3$) δ 12.6, 13.1, 13.3, 17.0, 17.1, 17.2, 17.3, 17.4, 17.5, 48.2, 55.5, 58.4, 64.7, 70.7, 75.0; HR-MS Calcd. For $(C_{18}H_{36}O_5Si_2+H)^+$ 389.2101. found 389.2171.

(+)-(6aS,6bR,7aR,8R,8aR)-8-Fluoro-2,2,4,4-tetraisopropylhexahydrooxireno[2',3':3,4]cyclo-penta[1,2-f][1,3,5,2,4]trioxadisilocine (13)

To a solution of compound 12 (11.5 g, 29.6 mmol) in anhydrous dichloromethane (DCM) diethylaminosulfur trifluoride (DAST) (19.0 ml, 118.5 mmol) was added slowly at −20° C., and warm the mixture to room temperature while stirring for 30 minutes. The reaction mixture was quenched with iced water at −20° C., the organic layer was collected and the aqueous phase was extracted with DCM (2×200 ml). Combined organic layer was dried over $Na_2SO_4$ and solvent removed under reduced pressure. The crude residue was purified by flash silica gel column chromatography (1% EtOAc/Hexane) to give 13 (6.1 g, 53.0%) as an oil. $[\alpha]^{24}_D$ +3.58° (c 1.0, $CHCl_3$); $^1H$ NMR (500 MHz, $CDCl_3$) δ 0.93-1.12 (m, 28H), 2.16 (m, 1H), 3.39 (s, 1H), 3.56 (dd, J=1.5, 3.0 Hz, 1H), 4.11-4.03 (m, 2H), 4.18-4.15 (m, 1H), 4.87 (dd, J=1.5, 5.5 Hz, 1H), 4.98 (dd, J=1.0, 5.0 Hz, 1H); $^{19}F$ NMR (500 MHz, $CDCl_3$) δ −201.77 (m); $^{13}C$ NMR (125 MHz, $CDCl_3$) δ 12.6, 13.1, 13.3, 16.6, 16.9, 17.0, 17.1, 17.3, 17.4, 17.5, 47.6, 52.4, 52.6, 54.9, 64.1, 75.6; HR-MS Calcd. For $(C_{18}H_{35}FO_4Si_2+H)^+$ 391.2058. found 391.1962.

(−)-(6aR,8R,9R,9aR)-9-Fluoro-2,2,4,4-tetraisopropyl-7-methylenehexahydrocyclopenta[f]-[1,3,5,2,4]trioxadisilocin-8-ol (14)

To a suspension of trimethylsulfonium iodide (30.5 g, 138.4 mmol) in THF (150 mL) at −20° C., n-BuLi (2.5 M solution in hexane) (55.3 mL, 138.4 mmol) was added. After 30 min, the epoxide 13 (6.0 g, 15.5 mmol) in THF (30 mL) was introduced at −20° C. and the reaction mixture allowed slowly to warm to 0° C. over 1 h. The mixture was then stirred at ambient temperature for 2 h, quenched with water and then extracted with ethyl acetate (3×200 ml). The combined organic layer was washed with brine, dried over $Na_2SO_4$ and concentrated reduced under pressure. The residues were purified on silica gel column chromatography (10% EtOAc/Hexane) to give the allylic alcohol 14 (5.1 g, 81%) as oil. $[\alpha]^{26}_D$ −0.54° (c 0.5, MeOH); $^1H$ NMR (500 MHz, $CDCl_3$) δ 0.93-1.12 (m, 28H), 1.99 (dd, J=2.5, 5.5 Hz, 1H, OH), 2.58 (m, 1H), 3.85 (dd, J=9.5, 11.5 Hz, 1H), 4.08 (dd, J=5.0, 12.0 Hz, 1H), 4.44 (m, 1H) 4.48 (m, 1H), 4.73 (dt, J=5.0, 9.0 Hz, 1H), 5.09 (s, 1H), 5.35-5.34 (m, 1H); $^{19}F$ NMR (500 MHz, $CDCl_3$) δ −203.0 (m); $^{13}C$ NMR (125 MHz, $CDCl_3$) δ 12.5, 12.9, 13.4, 13.5, 17.0, 17.03, 17.41, 17.46, 17.5, 17.6, 48.5, 50.2, 65.5, 72.6, 97.4 (d, J=185.0 Hz), 111.8, 146.8; HR-MS Calcd. For $(C_{19}H_{37}FO_4Si_2+H)^+$ 405.2214. found 405.2202.

(−)-(6aR,8S,9R,9aR)-9-Fluoro-2,2,4,4-tetraisopropyl-7-methylenehexahydrocyclopenta[f]-[1,3,5,2,4]trioxadisilocin-8-ol (15)

To a stirred solution of allylic alcohol 14 (5 g, 12.3 mmol) the Dess-martin periodinane reagent (7.8 g, 18.5 mmol) was added at 0° C. The mixture was warm to ambient temperature and stirred for 1 h. Mixture was passed through celite bed and the filtrate was concentrated under reduced pressure to give a crude allylic ketone, which was proceeded as such in next step without further purification. The crude ketone (4.5 g, 11.1 mmol) was dissolved in anhydrous methanol, cooled the solution at −78° C., $CeCl_3.7H_2O$ (5.5 g, 14.7 mmol) was added at −78° C., and then after 10 minutes stirring, $NaBH_4$ (0.54 g, 14.3 mmol) was added at one portion. After 15 min stirring at −78° C., the reaction mixture was allowed to reach 0° C., saturated solution of ammonium chloride (30 mL) and 10% aqueous solution of acetic acid were added, and then the mixture was allowed for 1 hr while stirring. Organic solvent was removed under reduced pressure and the residue was extracted with DCM (200 ml×2). The combined DCM extracts were washed with brine (50 mL×2), dried (anhydrous $Na_2SO_4$), filtered and concentrated under reduced pressure. The residue was purified by flash silica gel column chromatography (5% EtOAc/hexane) to give compound 15 (4.3 g, 86%) as oil. $[\alpha]^{D}_{26}$ −88.1° (c 0.5, MeOH); $^1H$ NMR (500 MHz, $CDCl_3$) δ 0.93-1.08 (m, 28H), 2.66 (s, 1H), 3.89 (dd, J=6.0, 11.5 Hz, 1H), 3.99 (dd, J=4.5, 12.0 Hz, 1H), 4.26-4.21 (m, 1H), 4.47 (dd, J=4.5, 13.5 Hz 1H), 4.65 (dt, J=8.0, 15.0 Hz, 1H), 5.16 (d, J=2.5 Hz, 1H), 5.35 (s, 1H); $^{19}F$ NMR (500 MHz, $CDCl_3$) δ −195.8 (m); $^{13}C$ NMR (125 MHz, $CDCl_3$) δ 12.5, 12.7, 13.3, 13.4, 16.9, 16.98, 17.07, 17.08, 17.4, 17.5, 49.1, 63.7, 73.7, 74.7, 102.3 (d, J=192.7 Hz), 111.5, 144.9, 150.0; HR-MS Calcd. For $(C_{19}H_{37}FO_4Si_2+H)^+$ 405.2214. found 405.2202.

(+)-9-[(1'R, 2'R, 3'R, 4'R)-2'-Fluoro-3',4'-methyl-(1,3,5,2,4)trioxadisilocine]-5'-methylene cyclopentan-1'-yl]-]6-N,N-dibocadenine (16)

To a stirred solution of triphenylphosphine (1.4 g, 5.56 mmol), in THF (20 mL) at −10° C., DIAD (1.12 mL, 5.56 mmol) was added drop wise and the reaction mixture was stirred at this temperature for 30 min. and then a solution of N,N-diboc protected adenine (1.5 g, 4.46 mmol) in THF (10 mL) was added and stirred for 30 minute at 0° C. Compound 15 (0.75 g, 1.85 mmol) in THF (5 mL) was then added and the reaction was stirred for 3 hours at room temperature. The solvent was removed under reduced pressure and the residue was purified by the silica gel column chromatography (EtOAc:hexane 1:20 to 1:10) to give 16 (0.87 g, 65%) as colorless oil. $[\alpha]^{26}_D$ +15.6° (c 1.0, $CHCl_3$); $^1H$ NMR (500 MHz, $CDCl_3$) δ 0.95-1.06 (m, 28H), 1.36 (s, 18H), 2.68 (m, 1H), 3.94 (dd, J=7.5, 11.5 Hz, 1H), 4.15 (dd, 4.5, 11.5 Hz, 1H), 4.53-4.47 (m, 1H), 4.81 (s, 1H), 4.94-4.91 (m, 2H), 5.04 (dt, J=4.5, 10.0 Hz, 1H), 5.22 (d, J=8.0 Hz, 1H), 5.82 (dd, J=4.5, 19.5 Hz, 1H), 8.07 (d, J=2.0 Hz, 1H), 8.80 (s, 1H); $^{19}F$ NMR (500 MHz, $CDCl_3$) δ −192.9 (m); $^{13}C$ NMR (125 MHz, $CDCl_3$) δ 12.4, 13.1, 13.2, 13.4, 16.90, 16.94, 17.0, 17.3, 17.4, 17.6, 21.7, 21.9, 27.7, 50.1, 69.9, 75.1, 84.4, 111.5, 128.2, 143.7, 144.8, 150.0, 153.8; HR-MS Calcd. For $(C_{34}H_{56}FN_5O_7Si_2+H)^+$ 722.3702. found 722.3770.

(+)-9-[(1'R, 2'R, 3'R, 4'R)-2'-Fluoro-3'-hydroxy-4'-(hydroxy methyl)-5'-methylenecyclo-pentan-1'-yl]-adenine (FMCA, 1)

To a solution of compound 16 (1.0 g, 1.38 mmol) in THF trifluoro acetic (0.10 mL, 1.80 mmol) was added and stirred for 16 h at ambient temperature. To this reaction mixture, tetrabutylammonium fluoride (TBAF, 1 M solution in THF) (1.3 ml, 1.38 mmol) was added and stirred at room temperature for 16 h. The solvent was removed under reduced pressure; the residue was dissolved in a mixture of isopropyl alcohol/chloroform (4:1, 200 ml) and washed with water (2×50 ml). The organic layer was collected, dried ($Na_2SO_4$), filtered and concentrated under reduced pressure. The residue was purified by column chromatography on silica gel (Methanol:DCM 1:10 to 4:10) to give 1 (0.33 g, 85%) as a white solid. mp: 215-218° C. (dec.) $[\alpha]^{25}_D$ +152.10° (c 0.5, MeOH); $^1H$ NMR (500 MHz, $CD_3OD$) δ 8.26 (s, 1H), 8.10 (d, J=2.5 Hz, 1H), 5.90 (d, J=2.5 Hz, 1H), 5.46 (s, 1H), 5.01-4.89 (m, 2H), 4.46-4.42 (m, 1H), 391-3.81 (m, 2H), 2.81 (bs, 1H); $^{19}F$ NMR (500 MHz, DMSO-$d_6$) δ −192.93 (m); $^{13}C$ NMR (125 MHz, $CD_3OD$) δ 156.0, 152.5, 149.9, 146.0, 141.1, (d, J=5.3 Hz), 117.8, 111.7, 109.8, 95.9 (d, J=184 Hz) 72.9 (d, J=23.6 Hz), 61.7, 57.5 (d, J=17.4 Hz), 51.0; Anal. Calcd. For $C_{12}H_{14}FN_5O_2$: C, 51.61; H, 5.05; N, 25.08. Found C, 51.74; H, 5.09; N, 24.92.

(−)-(6aR,8S,9S,9aR)-8-Bromo-9-fluoro-2,2,4,4-tetraisopropyl-7-methylenehexahydrocyclopenta[f][1,3,5,2,4]trioxadisilocine (17)

To a stirred solution of compound 14 (0.5 g, 1.23 mmol) in dry DCM carbon tetra bromide (0.46 ml, 4.9 mmol) was added drop wise, followed by the addition of triphenylphosphine (1.39 g, 4.9 mmol) at 0° C. The mixture was warmed to room temperature and stirred for 3 h. Reaction mixture was neutralized with triethyl amine and passed through a small bed of silica gel. The filtrate was concentrated on reduced pressure and the residue was purified by flash silica gel column chromatography (4% EtOAc/hexane) to give allyl bromide 17 (0.49 g, 86%) as oil. $^1$H NMR (500 MHz, $CDCl_3$) δ 0.93-1.01 (m, 28H), 2.65 (m, 1H), 3.87 (dd, J=4.5, 14.0 Hz, 1H), 3.96 (dd, J=4.0, 12.0 Hz, 1H), 4.11-4.07 (m, 1H), 4.61 (dd, J=2.0, 6.5 Hz, 1H), 4.95 (dt, J=7.0, 13.0 Hz, 1H), 5.22 (d, J=2.0 Hz, 1H), 5.40 (s, 1H); $^{19}$F NMR (500 MHz, $CDCl_3$) δ −187.0 (m); $^{13}$C NMR (125 MHz, $CDCl_3$) δ 11.50, 11.53, 11.7, 11.8, 12.2, 12.4, 15.8, 15.9, 16.02, 16.05, 16.2, 16.3, 16.4, 28.6, 47.8, 59.3, 101.1, 102.5, 113.6, 142.4; HR-MS Calcd. For $(C_{19}H_{36}BrFO_3Si_2+H)^+$ 467.1370. found 467.1411.

(+)-9-[(2'R,3'R, 4'R)-2'-Fluoro-3',4'-methyl-(1,3,5,2,4)trioxadisilocine]-5'-methylcyclopent-ene-6'-yl]-]-6-N,N-dibocadenine (18)

A mixture of 6-N,N-diboc-adenine (0.34 g, 2.5 mmol) and $K_2CO_3$ (0.17 g, 1.3 mmol) in 10 ml of dry DMF heated to 60° C. for 1 h. Cooled the mixture at 0° C. to which the compound 17 (0.4 g, 0.8 mmol) in the dry DMF was added drop wise. Then mixture was again heated to 60° C. for 4 h. The reaction was quenched with water and extracted with ethyl acetate (3×100 ml), and combined organic layer was washed with brine (2×50 ml), finally with water 50 ml, dried ($Na_2SO4$) and concentrated under reduced pressure. Residue was purified by column chromatography (2% MeOH/DCM) to give compound 18 (0.49 g, 78%) as oil. $^1$H NMR (500 MHz, $CDCl_3$) δ 0.86-1.03 (m, 28H), 1.38 (s, 18H), 2.64 (m, 1H), 3.79 (m, 1H), 4.08 (dd, J=4.0, 12.0 Hz, 1H), 4.42 (dt, J=5.0, 10 Hz, 1H), 4.80 (dd, J=3.5, 16.0 Hz, 2H), 5.26 (s, 1H), 5.36 (s, 1H), 8.00 (s, 1H), 8.80 (s, 1H); $^{19}$F NMR (500 MHz, $CDCl_3$) δ −174.1 (m); $^{13}$C NMR (125 MHz, $CDCl_3$) δ 12.5, 12.8, 13.35, 13.39, 16.93, 16.99, 17.0, 17.4, 17.5, 27.8, 42.2, 81.3, 83.8, 128.4, 150.0, 152.4.

REFERENCES (1) http://www.who.int/mediacentre/factsheets/fs204/en/.
(2) Bhattacharya, D.; Thio, C. L. *Clinical Infectious Diseases* 2010, 51, 1201.
(3) Kim, K. H.; Kim, N. D.; Seong, B. L. *Molecules* 2010, 15, 5878.
(4) Mukaide, M.; Tanaka, Y.; Shin-I, T.; Yuen, M. F.; Kurbanov, F.; Yokosuka, O.; Sata, M.; Karino, Y.; Yamada, G.; Sakaguchi, K.; Orito, E.; Inoue, M.; Baqai, S.; Lai, C. L.; Mizokami, M. *Antimicrob. Agents Ch* 2010, 54, 882.
(5) Bartholomeusz, A.; Locarnini, S. *Journal of Medical Virology* 2006, 78, S52.
(6) Wang, J. N.; Singh, U. S.; Rawal, R. K.; Sugiyama, M.; Yoo, J.; Jha, A. K.; Scroggin, M.; Huang, Z. H.; Murray, M. G.; Govindarajan, R.; Tanaka, Y.; Korba, B.; Chu, C. K. *Bioorg. Med. Chem. Lett.* 2011, 21, 6328.
(7) Rawal, R. K.; Singh, U. S.; Chavre, S. N.; Wang, J. N.; Sugiyama, M.; Hung, W.; Govindarajan, R.; Korba, B.; Tanaka, Y.; Chu, C. K. *Bioorg. Med. Chem. Lett.* 2013, 23, 503.
(8) Walsh, A. W.; Langley, D. R.; Colonno, R. J.; Tenney, D. J. *PLoS. One* 2010, 5.
(9) Jin, Y. H.; Liu, P.; Wang, J. N.; Baker, R.; Huggins, J.; Chu, C. K. *J Org. Chem.* 2003, 68, 9012.
(10) Jin, Y. H.; Chu, C. K. *Nucleos. Nucleot. Nucl.* 2003, 22, 771.
(11) Gadthula, S.; Rawal, R. K.; Sharon, A.; Wu, D.; Korba, B.; Chu, C. K. *Bioorg. Med. Chem. Lett.* 2011, 21, 3982.
(12) Vince, R.; Daluge, S.; Brownell, J. *J. Med. Chem.* 1986, 29, 2400.
(13) Vince, R.; Hua, M. *J. Med. Chem.* 1990, 33, 17.
(14) Daluge, S. M.; Martin, M. T.; Sickles, B. R.; Livingston, D. A. *Nucleos. Nucleot. Nucl.* 2000, 19, 297.
(15) Corey, E. J.; Achiwa, K. *J. Am. Chem. Soc.* 1969, 91, 1429.
(16) Mahmoudian, M.; Lowdon, A.; Jones, M.; Dawson, M.; Wallis, C. *Tetrahedron-Asymmetr*. 1999, 10, 1201.
(17) Slama, J. T.; Mehta, N.; Skrzypczak-Jankun, E. *J. Org. Chem.* 2006, 71, 7877.
(18) Claiborne, C. In US Patent United State; Vol. PCT/US2007/017463.
(19) Grainger, R. S.; Patel, A. *Chem. Commun.* 2003, 1072.
(20) Lakshmipathi, P.; Gree, D.; Gree, R. *Org. Lett.* 2002, 4, 451.
(21) Alcaraz, L.; Cridland, A.; Kinchin, E. *Org. Lett.* 2001, 3, 4051.
(22) Luche, J. L. *J. Am. Chem. Soc.* 1978, 100, 2226.

The invention claimed is:
1. A process for synthesizing the compound of formula 1:

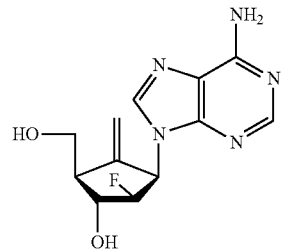

comprising the steps of:
(a) diazotization of the amine of formula 8:

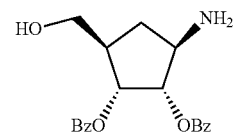

followed by an elimination reaction to produce the alkene of formula 9:

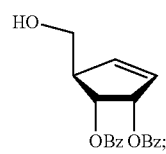

(b) removing the benzoyl protecting groups on the 2' and 3' hydroxyl positions of compound 9 and protecting the 3' and 5' hydroxyl groups with a 1,1,3,3-tetraisopropyldisiloxane protecting group;

(c) stereoselective epoxidation of the silyl protected compound obtained from step (b) followed by fluorination to yield the cis-fluoro-β-epoxide of formula 13:

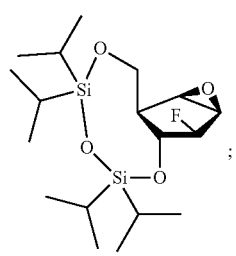

13

(d) selective opening of the cis-fluoro-β-epoxide of formula 13 and introduction of a methylene group to yield D-2'-fluoro-6'-methylene cyclopentenol of formula 15:

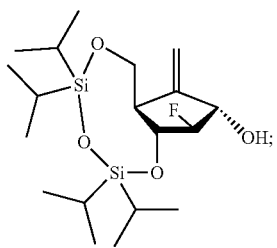

15

(e) coupling D-2'-fluoro-6'-methylene cyclopentenol of formula 15 with protected adenine using diisopropyl azodicarboxylate (DIAD) and triphenylphosphine (TPP) in THF to produce a compound of formula 16, where P represents amine protecting group(s):

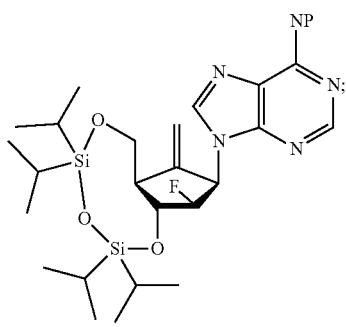

16 and (f) removing P and the 1,1,3,3-tetraisopropyldisiloxane protecting group of the compound of formula 16 to yield the compound of formula 1;

wherein the process can be done in one pot or in steps.

2. The method of claim 1 wherein P represents N-tert-butyloxycarbonyl protecting groups.

\* \* \* \* \*